United States Patent
Hsiao

(10) Patent No.: US 12,090,477 B2
(45) Date of Patent: Sep. 17, 2024

(54) SYSTEM AND METHOD FOR DETECTING BIOMOLECULES

(71) Applicant: TAIWAN SEMICONDUCTOR MANUFACTURING COMPANY LTD., Hsinchu (TW)

(72) Inventor: Yi-Hsing Hsiao, Hsinchu (TW)

(73) Assignee: TAIWAN SEMICONDUCTOR MANUFACTURING COMPANY LTD., Hsinchu (TW)

( * ) Notice: Subject to any disclaimer, the term of this patent is extended or adjusted under 35 U.S.C. 154(b) by 755 days.

(21) Appl. No.: 17/193,454

(22) Filed: Mar. 5, 2021

(65) Prior Publication Data
US 2022/0280935 A1 Sep. 8, 2022

(51) Int. Cl.
*B01L 3/00* (2006.01)
*G01N 27/414* (2006.01)
*G01N 33/543* (2006.01)

(52) U.S. Cl.
CPC ... *B01L 3/502707* (2013.01); *B01L 3/502715* (2013.01); *G01N 27/4145* (2013.01); *G01N 33/54373* (2013.01); *B01L 2300/0816* (2013.01); *B01L 2300/123* (2013.01)

(58) Field of Classification Search
CPC ............. G01N 27/414; G01N 27/4145; G01N 33/54373; B01L 3/502707; B01L 3/502715; B01L 2300/0816; B01L 2300/123
See application file for complete search history.

(56) References Cited

U.S. PATENT DOCUMENTS

| | | | |
|---|---|---|---|
| 10,161,901 B2 | 12/2018 | Huang et al. | |
| 2011/0165557 A1 | 7/2011 | Ah et al. | |
| 2019/0369044 A1* | 12/2019 | Chang | G01N 27/4146 |

(Continued)

FOREIGN PATENT DOCUMENTS

| | | | | |
|---|---|---|---|---|
| AT | 398133 B | * | 9/1994 | G01N 27/414 |
| CN | 101126735 A | | 2/2008 | |
| CN | 101592627 A | | 12/2009 | |

(Continued)

OTHER PUBLICATIONS

EPO machine-generated English language translation of WO 2005/090961, patent published Sep. 25, 2005 (Year: 2005).*
EPO machine-generated English language translation of AT 398133 B, patent published Sep. 26, 1994 (Year: 1994).*
US 2019369044 A1 is the US counterpart of CN 110554177 A.

(Continued)

*Primary Examiner* — Alexander S Noguerola
(74) *Attorney, Agent, or Firm* — WPAT LAW; Anthony King

(57) ABSTRACT

A system and a method for detecting biomolecules are provided. The method comprises disposing a first coating layer associated with a first target biomolecule on a first portion of a sensing film of a sensor and disposing a second coating layer associated with the first target biomolecule on the first portion of the sensing film. The method further comprises measuring a baseline electrical signal associated with a buffer solution by the sensor, disposing a first analyte solution on the sensor, and measuring the first electrical signal associated with the first analyte solution. The method further comprises determining whether the first target biomolecule are detected in the first analyte solution based on a comparison between the measured first electrical signal and a first threshold.

20 Claims, 12 Drawing Sheets

(56) References Cited

U.S. PATENT DOCUMENTS

2021/0010972 A1  1/2021  Dobrokhotov et al.

FOREIGN PATENT DOCUMENTS

| CN | 101309670 B | 2/2011 | | |
|---|---|---|---|---|
| CN | 107064271 A | 8/2017 | | |
| CN | 107356649 A | 11/2017 | | |
| CN | 110554177 A | 12/2019 | | |
| CN | 112326074 A | 2/2021 | | |
| KR | 1020210012454 A | 2/2021 | | |
| TW | I689720 B | 4/2020 | | |
| TW | 202020440 A | 6/2020 | | |
| WO | WO 2005090961 A1 * | 9/2005 | ........... | G01N 27/414 |

OTHER PUBLICATIONS

US 2017160226 A1 is the US counterpart of CN 107064271 A.

English Abstract Translation of Foreign Reference CN 101126735 A.

English Abstract Translation of Foreign Reference CN 101592627 A.

English Abstract Translation of Foreign Reference CN 107356649 A.

English Abstract Translation of Foreign Reference CN 112326074 A.

English Abstract Translation of Foreign Reference KR 20210012454 A.

* cited by examiner

SYSTEM AND METHOD FOR DETECTING BIOMOLECULES

BACKGROUND

The present disclosure relates, in general, to systems and methods for detecting or sensing biomolecules. Specifically, the present disclosure relates to systems and methods for detecting immunization and hybridization on the basis of electronic detection principles.

The identification of biomolecules has led to the major aspect of disease diagnosis. Some critical diseases like cancer can be identified with an increased level of protein markers like vascular endothelial growth factor (VEGF) is a well-known cancer marker. Moreover, viruses and bacterial cells are known to be the major causes of disease which can also be detected with the help of proteins present on their surface. Various optical sensing techniques for detection of biomolecules are developed. Although existing techniques for detecting target biomolecules on the basis of optical detection principles have good detection sensitivity, they can be considerably time-consuming. Biosensors that include transistors are sensors that electrically sense charges, photons, and mechanical properties of bio-entities or biomolecules. The sensor detects the concentration of bio-entities or biomolecules via the interaction between specified reactants and bio-entities/biomolecules. Such biosensors are fast in signal conversion, can be manufactured using semiconductor processes, and be easily applied to integrated circuits and MEMS. A bio-FET sensor can be created to detect various types of biomolecules, including, for example, H+, Ca2+, DNA, proteins and glucose.

BRIEF DESCRIPTION OF THE DRAWINGS

Aspects of the embodiments of the present disclosure are best understood from the following detailed description when read with the accompanying figures. It should be noted that, in accordance with the standard practice in the industry, various structures are not drawn to scale. In fact, the dimensions of the various structures may be arbitrarily increased or reduced for clarity of discussion.

DETAILED DESCRIPTION

Figure 1B:
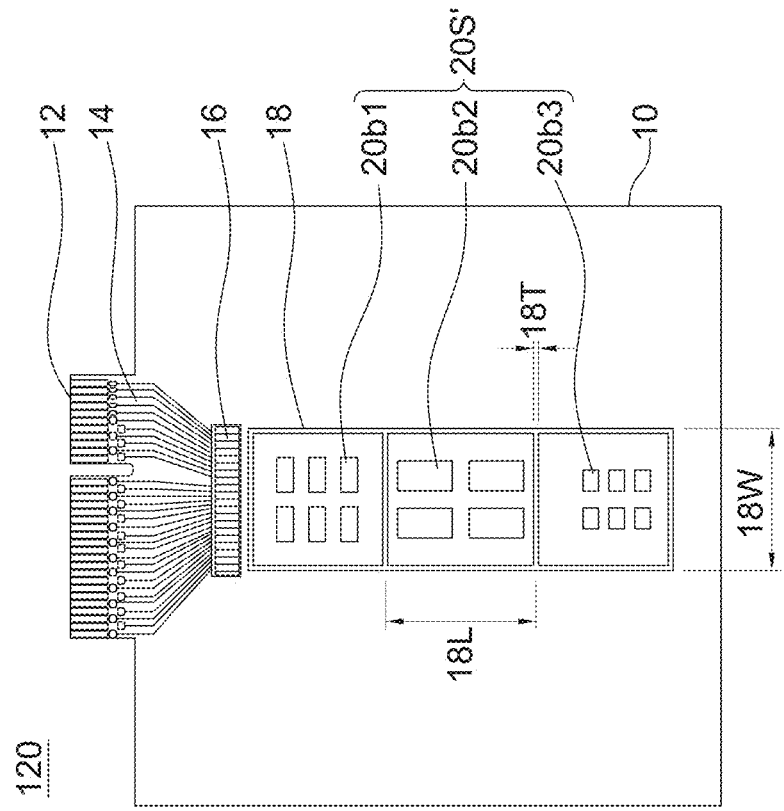
FIG. 1B illustrates a top view of a semiconductor device in accordance with some embodiments of the present disclosure.

The following disclosure provides many different embodiments, or examples, for implementing different features of the provided subject matter. Specific examples of elements and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "over," "upper," "on" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

As used herein, although terms such as "first," "second" and "third" describe various elements, components, regions, layers and/or sections, these elements, components, regions, layers and/or sections should not be limited by these terms. These terms may only be used to distinguish one element, component, region, layer or section from another. Terms such as "first," "second" and "third" when used herein do not imply a sequence or order unless clearly indicated by the context.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in the respective testing measurements. Also, as used herein, the terms "substantially," "approximately" and "about" generally mean within a value or range that can be contemplated by people having ordinary skill in the art. Alternatively, the terms "substantially," "approximately" and "about" mean within an acceptable standard error of the mean when considered by one of ordinary skill in the art. People having ordinary skill in the art can understand that the acceptable standard error may vary according to different technologies. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the terms "substantially," "approximately" or "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

Figure 1A:
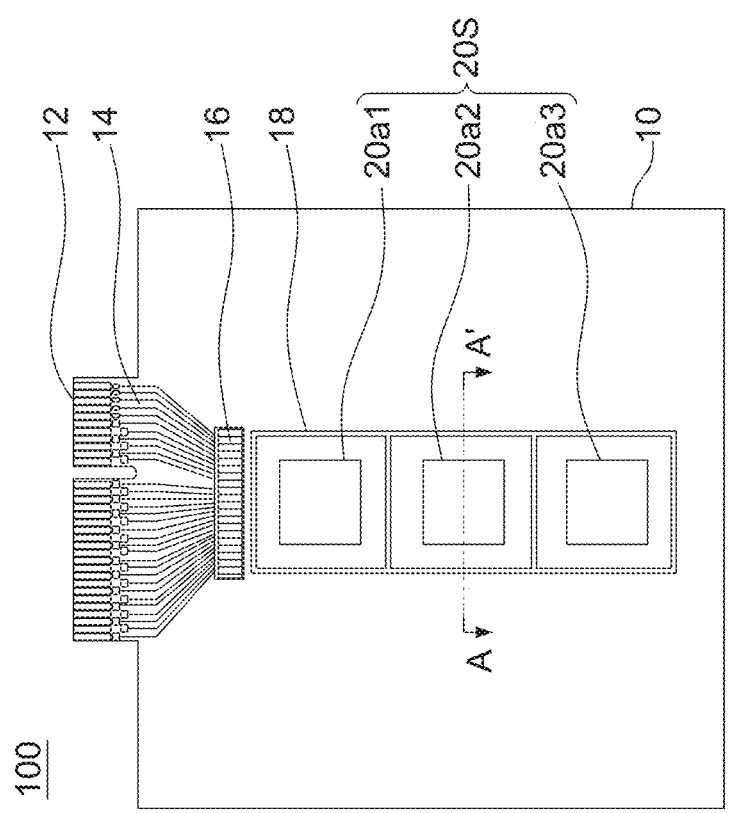
FIG. 1A illustrates a top view of a semiconductor device, in accordance with some embodiments of the present disclosure.

FIG. 1A illustrates a top view of a semiconductor device, in accordance with some embodiments of the present disclosure.

FIG. 1A shows a device 100. The device 100 can be an electrical device. The device 100 can be a system of integrated circuits (IC). The device 100 can include a sensor 20S disposed on a printed circuit board (PCB) 10. The sensor 20S may include sensing regions 20$a$1, 20$a$2 and 20$a$3. In some embodiments, the sensing regions 20$a$1, 20$a$2 and 20$a$3 can have identical dimensions/sizes. In some embodiments, the sensing regions 20$a$1, 20$a$2 and 20$a$3 can have different dimensions/sizes.

The number of sensing regions is not limited to three. In some embodiments, the sensor 20S may include more than three sensing regions. In some embodiments, the sensor 20S may include only two sensing regions, or only one sensing region.

The sensing regions 20$a$1, 20$a$2 and 20$a$3 can be surrounded by a separating structure 18. The sensing regions 20$a$1, 20$a$2 and 20$a$3 can be separated by the separating structure 18. The separating structure 18 may form individual spaces for each of the sensing regions 20$a$1, 20$a$2 and 20$a$3. The separating structure 18 may form tanks for each of the sensing regions 20$a$1, 20$a$2 and 20$a$3.

The device 100 includes conductive contacts 12 and 16. The conductive contacts 12 can be electrically coupled with the conductive contacts 16 through interconnections 14. The conductive contacts 16 can be electrically connected to the sensor 20S. The conductive contacts 16 can be electrically coupled with the sensing regions 20$a$1, 20$a$2 and 20$a$3. Currents or voltages can be applied to the conductive contacts 12. Signals or commands can be communicated between the conductive contacts 12 and 16. Signals or commands can be communicated between the conductive contacts 12 and the sensing regions 20$a$1, 20$a$2 and 20$a$3. The sensor 20S can be operated based on the currents or voltages applied to the conductive contacts 12. The sensing regions 20$a$1, 20$a$2 and 20$a$3 can be operated based on the signals or commands applied to the conductive contacts 12.

The sensing regions 20$a$1, 20$a$2 and 20$a$3 can be used to detect different biomolecules simultaneously. The sensing regions 20$a$1, 20$a$2 and 20$a$3 can be used to detect identical biomolecules with different dosages at the same time.

In some embodiments, the separating structure 18 may include a silicon-based organic polymer. In some embodiments, the separating structure 18 may include Polydimethylsiloxane (PDMS). In some embodiments, the separating structure 18 may include silica gel. In some embodiments, the separating structure 18 may include any type of material that is suitable for holding liquids.

FIG. 1B illustrates a top view of a semiconductor device in accordance with some embodiments of the present disclosure. FIG. 1B shows a device 120. The device 120 can be an electrical device. The device 120 can be a system of ICs. The device 120 can include a sensor 20S' disposed on a PCB 10. The device 120 of FIG. 1B is similar to the device 100 of FIG. 1A, except for the sensing regions of sensor 20S' being different from those of the sensor 20S.

The sensor 20S' include sensing regions 20$b$1. The sensor 20S' include sensing regions 20$b$2. The sensor 20S' include sensing regions 20$b$3. The sensing regions 20$b$1, 20$b$2 and 20$b$3 can have different sizes/dimensions. The number of the sensing regions 20$b$1, 20$b$2 and 20$b$3 can be different. In some embodiments, the number of the sensing regions 20$b$1, 20$b$2 and 20$b$3 can be identical. The sensing regions 20$b$1, 20$b$2 and 20$b$3 can be used to detect different biomolecules simultaneously. The sensing regions 20$b$1, 20$b$2 and 20$b$3 can be used to detect identical biomolecules with different dosages at the same time.

The separating structure 18 can have a thickness 18T. In some embodiments, the thickness 18T can range from approximately 0.05 cm to 0.5 cm. The separating structure 18 surrounding the sensing region 20$b$2 can have a length 18L and a width 18W. In some embodiments, the length 18L can range from approximately 0.05 cm to 0.5 cm. In some embodiments, the width 18W can range from approximately 0.05 cm to 0.5 cm.

The ratios between the length 18L, the width 18W, and the thickness 18T may have specific ranges. In some embodiments, the ratio of the length 18L to the width 18W can range from 1 to 3. The ratio of the length 18L to the thickness 18T can range from 5 to 10. The ratio of the width 18W to the thickness 18T can range from 5 to 10.

Figure 2:
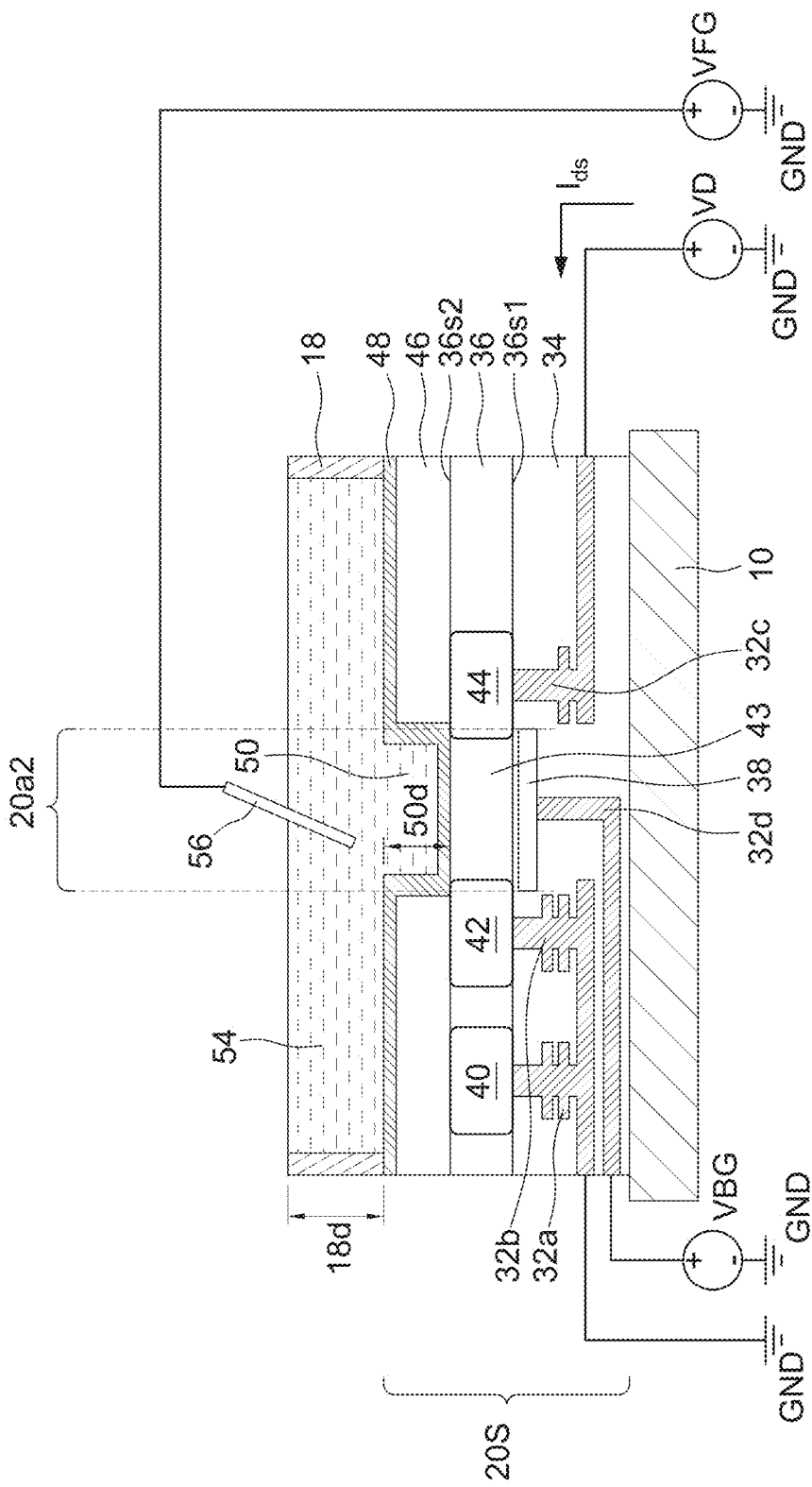
FIG. 2 illustrates a cross-sectional view of a semiconductor device, along the dotted-line A-A' of FIG. 1A, in accordance with some embodiments of the present disclosure.

FIG. 2 illustrates a cross-sectional view of a semiconductor device, along the dotted-line A-A' of FIG. 1A, in accordance with some embodiments of the present disclosure.

FIG. 2 shows a cross-sectional view of the sensor 20S, along the dotted-line A-A' of FIG. 1A. The sensor 20S disposed on the PCB 10 includes a dielectric layer 34, a substrate 36, a buried oxide (BOX) layer 46, and a sensing film 48. Base electrode 40, source electrode 42 and drain electrode 44 can be embedded within the substrate 36. A bottom gate electrode 38 is embedded within the dielectric layer 34. Interconnect layers 32$a$, 32$b$, 32$c$ and 32$d$ can be disposed within the dielectric layer 34. The interconnect layer 32$a$ can be electrically coupled between the base electrode 40 and the ground (GND). The interconnect layer 32$b$ can be electrically coupled between the source electrode 42 and GND. The interconnect layer 32$c$ can be electrically coupled between the drain electrode 44 and a drain voltage VD. The interconnect layer 32$d$ can be electrically coupled between the bottom gate electrode 38 and a bottom gate voltage VBG.

In some embodiments, the dielectric layer 34 may include silicon oxide. Another exemplary dielectric layer 34 includes silicon nitride, silicon oxynitride, a dielectric with a high dielectric constant (high k), and/or combinations thereof. Examples of high k materials include hafnium silicate, hafnium oxide, zirconium oxide, aluminum oxide, tantalum pentoxide, hafnium dioxide-alumina ($HfO_2Al_2O_3$) alloy, or combinations thereof.

The substrate 36 has a first side 36$s$1 and a second side 36$s$2 opposite to the first side. The substrate 36 may be a semiconductor substrate (e.g., wafer). The substrate 36 may be a silicon substrate. Alternatively, the substrate 36 may include another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In some embodiments, the substrate 36 can be a semiconductor on insulator (SOI) substrate. The substrate 36 may include doped regions, such as p-wells and n-wells.

The base electrode 40, source electrode 42, drain electrode 44, and/or channel region 43 are formed on an active region of the substrate 36. The sensor 20S can be an n-type FET (nFET) or a p-type FET (pFET). For example, the source/drain electrodes 42 and 44 may include n-type dopants or p-type dopants depending on the FET configuration. The bottom gate electrode 38 is disposed adjacent to the first side 36s1 of the substrate 36, and functions as a control gate. In some embodiment, the bottom gate electrode 38 may include polysilicon. In some embodiments, the bottom gate electrode 38 may include material such as, Cu, W, Ti, Ta, Cr, Pt, Ag, Au, or suitable metallic compounds like TiN, TaN, NiSi, CoSi, or combinations thereof.

The BOX layer 46 can be formed by a process such as separation by implanted oxygen (SIMOX), and/or other suitable processes. An opening 50 is formed at the second side 36s2 of the substrate 36. The opening 50 may include a trench formed in one or more layers disposed on the second side 36s2 of the substrate 36. The opening 50 can be formed above the channel region 43. The opening 50 may be formed using suitable photolithography processes to provide a pattern on the substrate, and etching processes to remove materials from the buried oxide layer 46 until the second side 36s2 of the substrate 36 is exposed. The etching processes include wet etch, dry etch, plasma etch and/or other suitable processes.

The opening 50 includes a depth 50d. In some embodiments, the depth 50d can be approximately 1 micron. In some embodiments, the depth 50d can range from approximately 0.5 microns to 3 microns. In some embodiments, the depth 50d can range from approximately 0.1 microns to 10 microns.

A sensing film 48 is formed conformingly to the BOX layer 46 and the opening 50. The sensing film 48 is deposited over the sidewalls and bottom of opening 50. The sensing film 48 is able to bind with biomolecules or bio-entities. For example, the sensing film 48 may provide a binding interface for biomolecules or bio-entities. The sensing film 48 may include a dielectric material, a conductive material, and/or other suitable material for holding a receptor. Exemplary sensing materials include high-k dielectric films, metals, metal oxides, dielectrics, and/or other suitable materials. As a further example, exemplary sensing materials include HfO2, Ta2O5, Pt, Au, W, Ti, Al, Cu, oxides of such metals, SiO2, Si3N4, Al2O3, TiO2, TiN, SnO, SnO2, SrTiO3, ZrO2, La2O3; and/or other suitable materials. The sensing film 48 may be formed using CMOS processes such as, for example, physical vapor deposition (PVD) (sputtering), chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer deposition (ALD). In some embodiments, the sensing film 48 may include a plurality of layers. A receptor such as an enzyme, antibody, ligand, peptide, nucleotide, cell of an organ, organism, or piece of tissue is placed on the sensing film 48 for detection of a target biomolecule.

A reference electrode 56 can be placed in the analyte solution 54, functioning as a control gate. The reference electrode 56 can be disposed adjacent to the second side 36s2 of the substrate 36.

The reference electrode 56 can be electrically coupled with a fluidic gate voltage VFG. In some embodiments, the sensing film 48 is exposed to the analyte solution 54, and the reference electrode 56 is immersed in the analyte solution 54 such that the reference electrode 56 is a fluidic gate. The surface potential change of the reference electrode 56 modulates the threshold voltage ($V_{TH}$) of the sensor 20S through capacitive coupling.

When the reference electrode 56 is triggered by the presence of biomolecules, the sensor 20S will transfer electrons and induce the field effect charging of the bottom gate electrode 38, thereby modulating the current (e.g., Ids). The change of the current or threshold voltage ($V_{TH}$) can serve to indicate detection of the relevant biomolecules or bio-entities.

The separating structure 18 is disposed above and in contact with the sensing film 48. The separating structure 18 can form a tank surrounding the sensing region 20a2. The tank formed by the separating structure 18 can have a depth 18d. In some embodiments, the depth 18d can range from approximately 0.05 cm to 0.5 cm.

The separating structure 18 can maintain the analyte solution 54 within a specific region of the sensor 20S. The separating structure 18 can prevent the analyte solution 54 from leaking out of a specific region of the sensor 20S. The separating structure 18 can maintain the analyte solution 54 within the sensing region 20a2 of the sensor 20S.

Figure 3A:
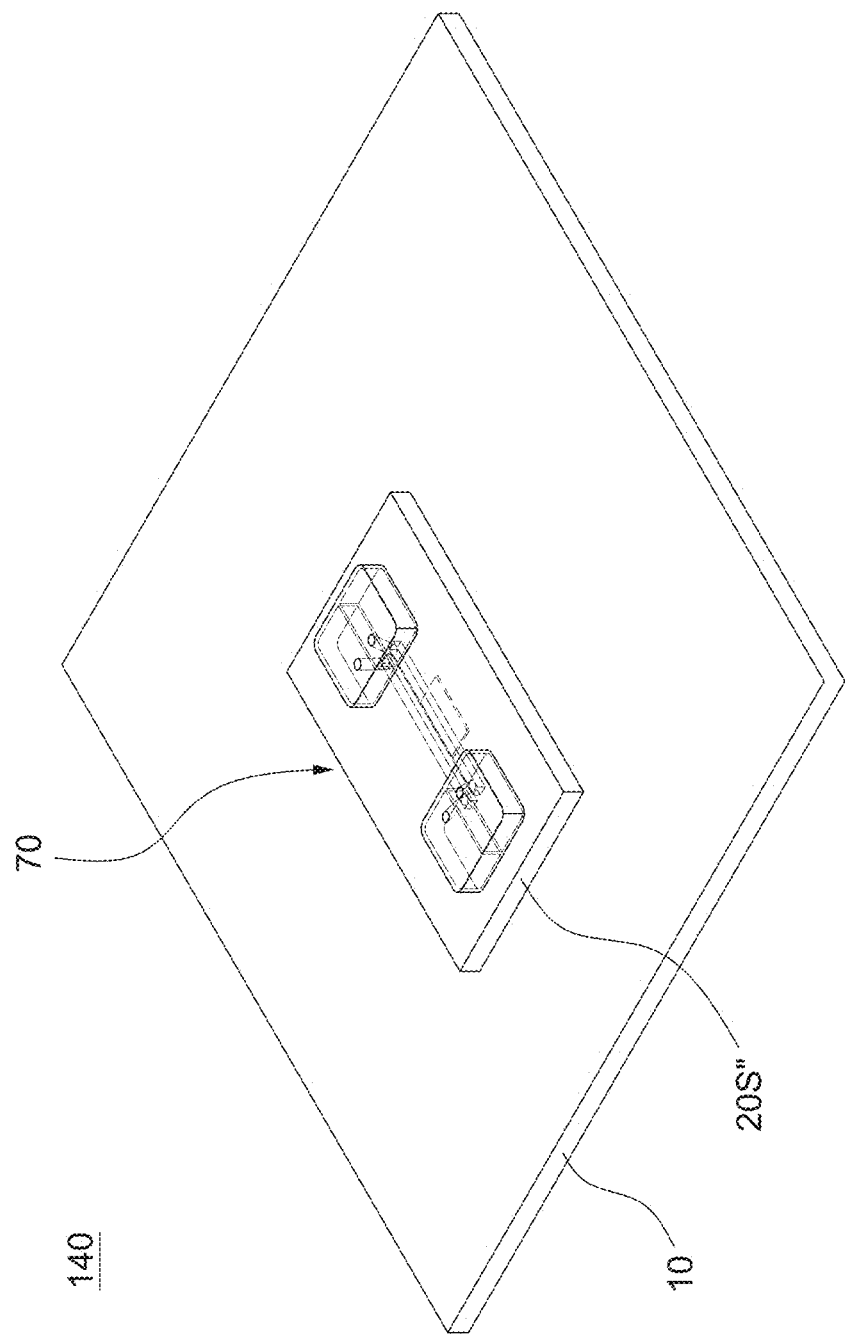
FIG. 3A illustrates a three-dimensional view of a semiconductor device, in accordance with some embodiments of the present disclosure.

FIG. 3A illustrates a three-dimensional view of a semiconductor device, in accordance with some embodiments of the present disclosure. FIG. 3A shows a device 140. The device 140 can be an electrical device. The device 140 can be a system of ICs. The device 140 can include a sensor 20S" disposed on a PCB 10. The device 140 further includes a polydimethylsiloxane (PDMS) microfluidic system 70 integrated on the sensor 20S". The PDMS microfluidic system 70 can be disposed above the sensor 20S". The PDMS microfluidic system 70 can be fixed to the sensor 20S". The PDMS microfluidic system 70 can be attached to the sensor 20S".

Figure 3B:
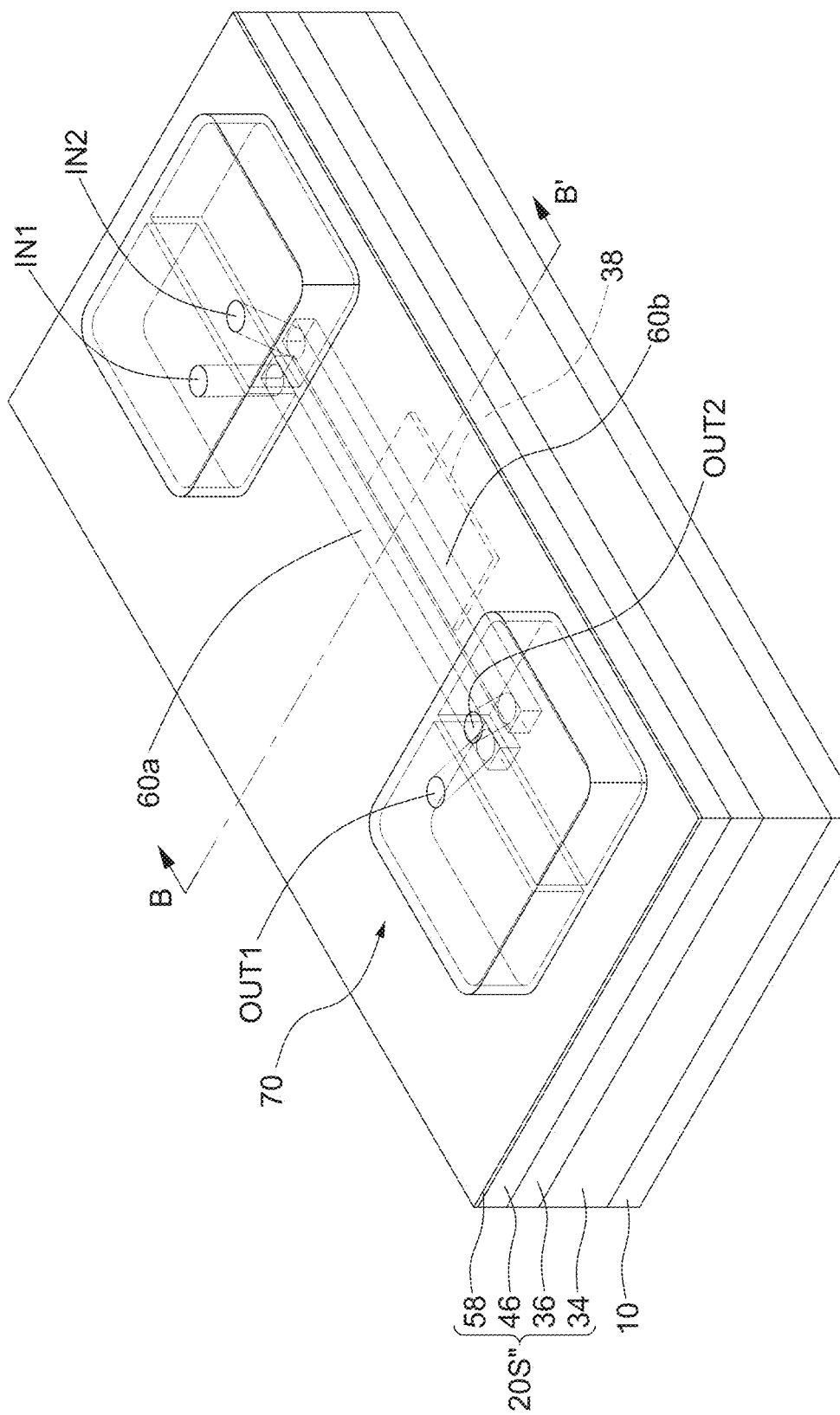
FIG. 3B illustrates an enlarged view of a semiconductor device, in accordance with some embodiments of the present disclosure.

FIG. 3B illustrates an enlarged view of a semiconductor device, in accordance with some embodiments of the present disclosure. FIG. 3B shows an enlarged view of the PDMS microfluidic system 70 integrated on the sensor 20S". The PDMS microfluidic system 70 includes two inlets IN1 and IN2 and two outlets OUT1 and OUT2. The inlet IN1 is connected to the outlet OUT1 through a channel 60a. The inlet IN2 is connected to the outlet OUT2 through a channel 60b. Liquids can be filled to the channels 60a and 60b through the inlets IN1 and IN2, respectively.

The biomolecules within the channels 60a or 60b can be sensed or detected by the bottom gate electrode 38. The channel 60a is isolated from the channel 60b. The channel 60a is separated from the channel 60b. The channel 60a can be used to detect a first type of biomolecules. The channel 60b can be used to detect a second type of biomolecules. The channels 60a and 60b can be used to simultaneously detect biomolecules of different types.

The number of channels included by the PDMS microfluidic system 70 is not limited to that shown in FIG. 3B. In some embodiments, the PDMS microfluidic system 70 may include more than two channels. With more isolated channels, more types of biomolecules can be detected by the sensor 20S" at the same time.

The sensor 20S" disposed on the PCB 10 includes the dielectric layer 34, substrate 36, BOX layer 46 and sensing film 58. The structure of the PDMS microfluidic system 70 integrated on the sensor 20S" will be further illustrated in accordance with FIG. 4.

Figure 4:
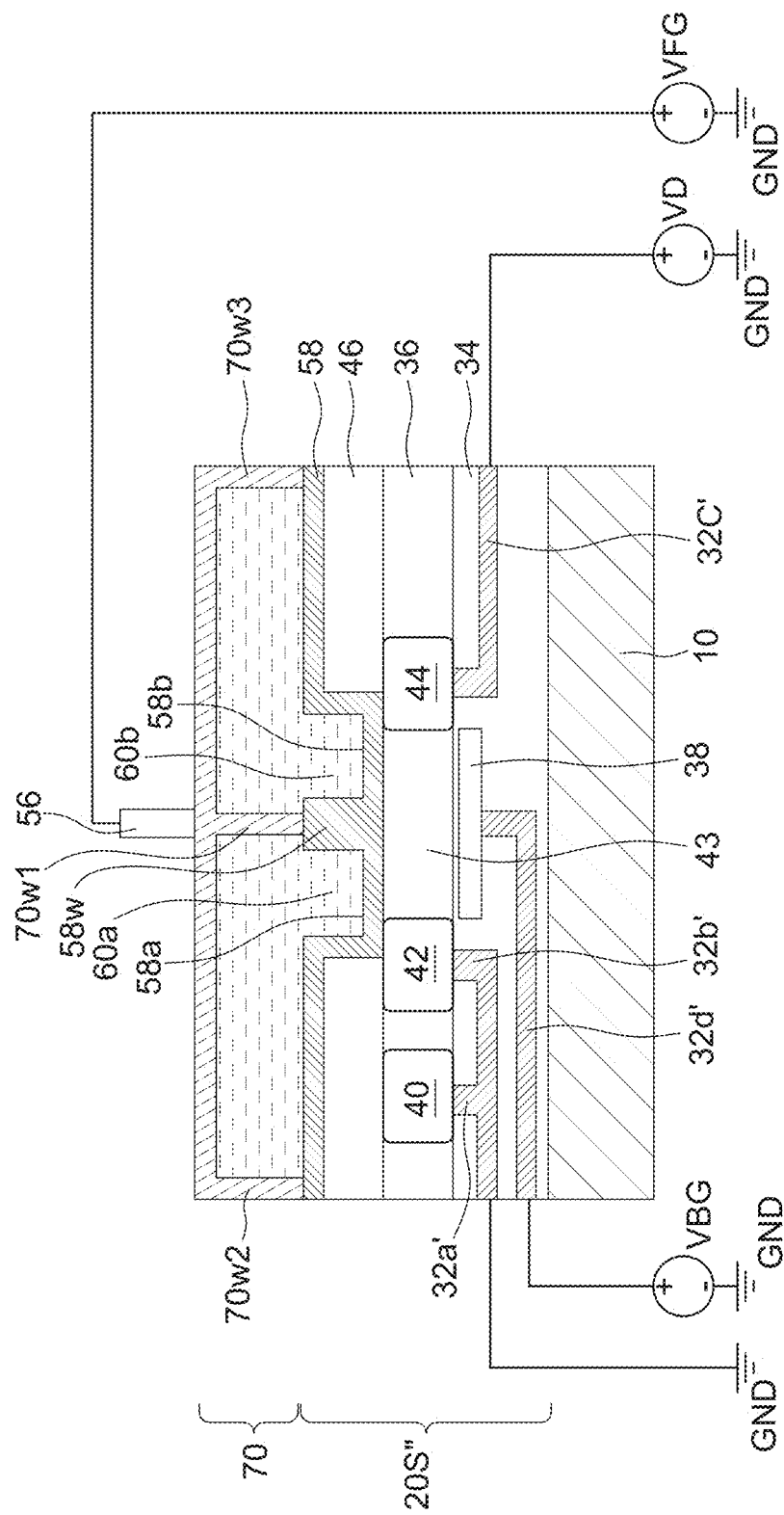
FIG. 4 illustrates a cross-sectional view of a semiconductor device, along the dotted-line B-B' of FIG. 3B, in accordance with some embodiments of the present disclosure.

FIG. 4 illustrates a cross-sectional view of a semiconductor device, along the dotted-line B-B' of FIG. 3B, in accordance with some embodiments of the present disclosure.

The sensor 20S" includes the dielectric layer 34, substrate 36, BOX layer 46 and sensing film 58. The sensor 20S" of FIG. 4 is similar to the sensor 20S of FIG. 2, except that the separating structure 18 of the sensor 20S is replaced by the PDMS microfluidic system 70. In addition, the opening 50 of the sensor 20S is replaced by the channels 60a and 60b.

Although the interconnect layers 32a', 32b', 32c', and 32d' of the sensor 20S" are drawn with different profiles than the interconnect layers 32a, 32b, 32c, and 32d of the sensor 20S, it can be contemplated that the interconnect layers 32a', 32b', 32c', and 32d' of the sensor 20S" can function similar to the interconnect layers 32a, 32b, 32c, and 32d of the sensor 20S.

The sensing film 58 can be formed conformingly to the BOX layer 46, and includes a wall structure 58w. The wall structure 58w can be connected to the wall structure 70w1 of the PDMS microfluidic system 70. The wall structures 58w and 70w1 can separate the channel 60a from the channel 60b. The wall structures 58w and 70w1 can isolate the channel 60a from the channel 60b. The channel region 43 can be formed between the source/drain electrodes 42 and 44. The channels 60a and 60b can be disposed above the channel region 43.

The sensing film 58 can include a first portion 58a and a second portion 58b. The first portion 58a can be located on a first side of the wall structure 58w. The second portion 58b can be located on a second side of the wall structure 58w opposite the first side.

In addition to the wall structure 70w1, the PDMS microfluidic system 70 includes wall structures 70w2 and 70w3. The wall structures 70w1, 70w2 and 70w3 can also be referred to as separating structures. The wall structure 70w2 can surround the first portion 58a of the sensing film 58. The wall structure 70w3 can surround the second portion 58b of the sensing film 58. The wall structure 70w2 can surround a portion of the sensor 20S". The wall structure 70w3 can surround a portion of the sensor 20S".

The reference electrode 56 can be disposed in the inlets IN1 or IN2. The reference electrode 56 can be disposed in the outlets OUT1 or OUT 2.

Figure 5A:
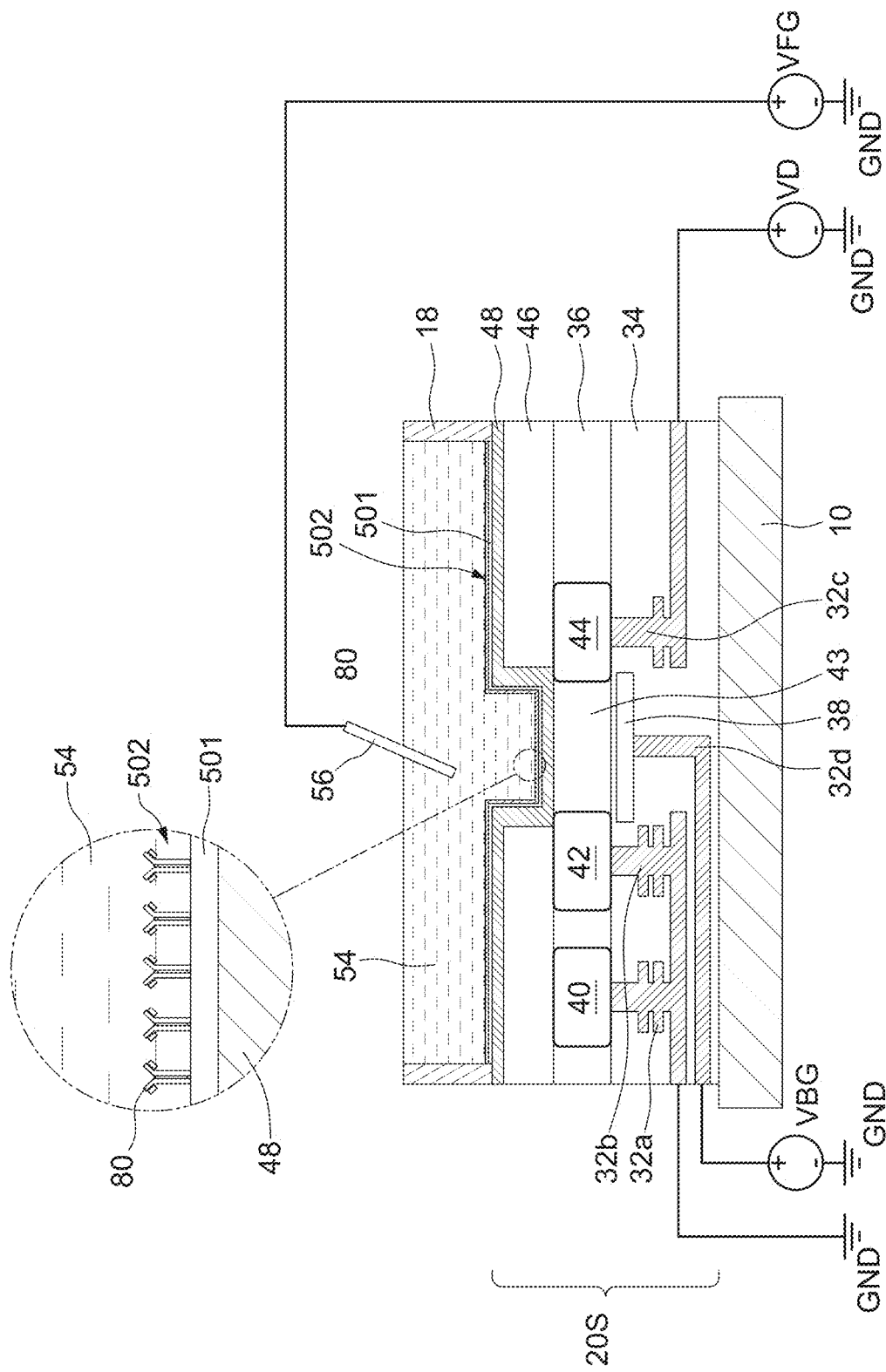
FIGS. 5A, 5B and 5C illustrate exemplary operations for detecting target biomolecules on the basis of electronic detection principles, in accordance with some embodiments of the present disclosure.
Figure 5B:
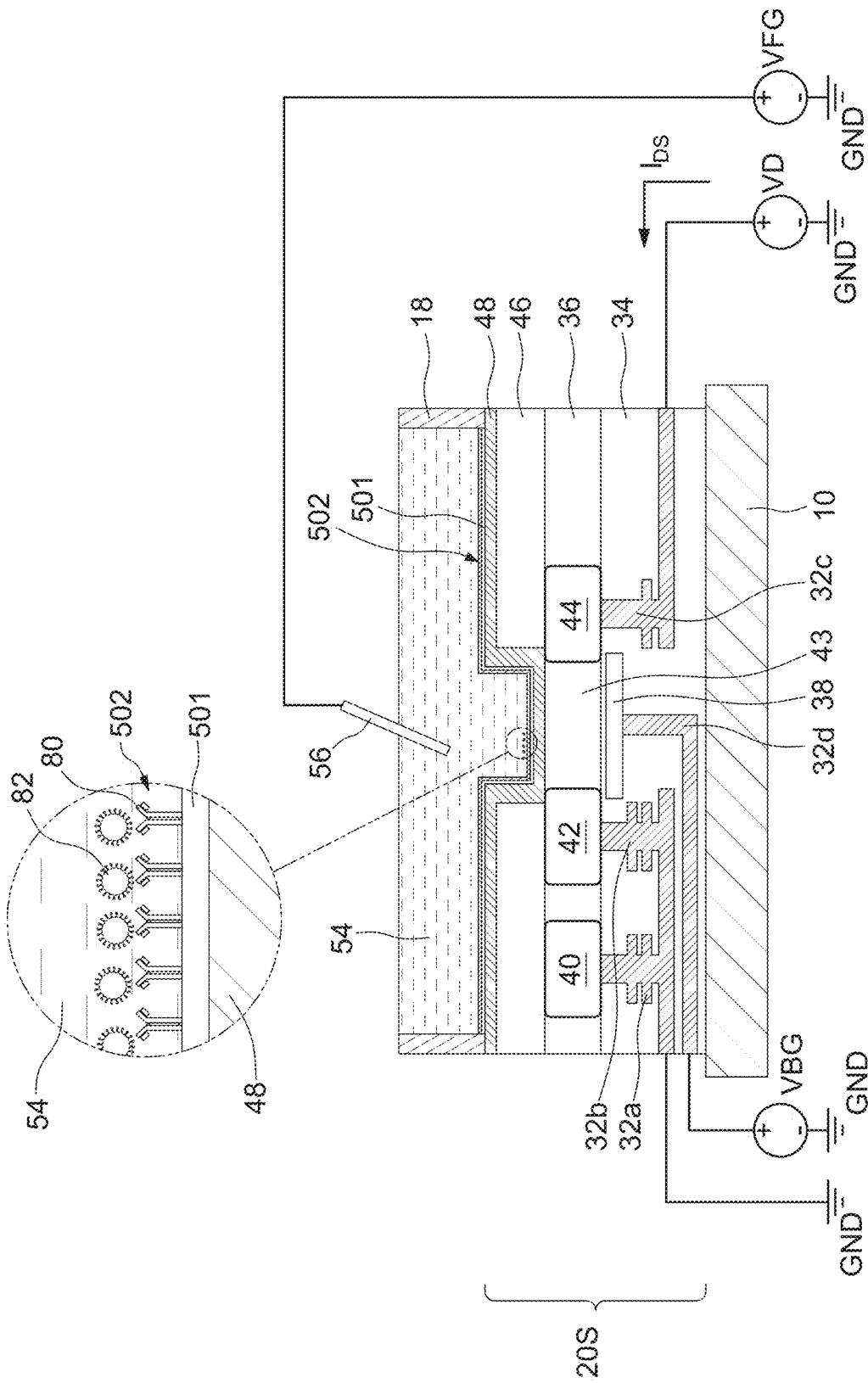
Figure 5C:
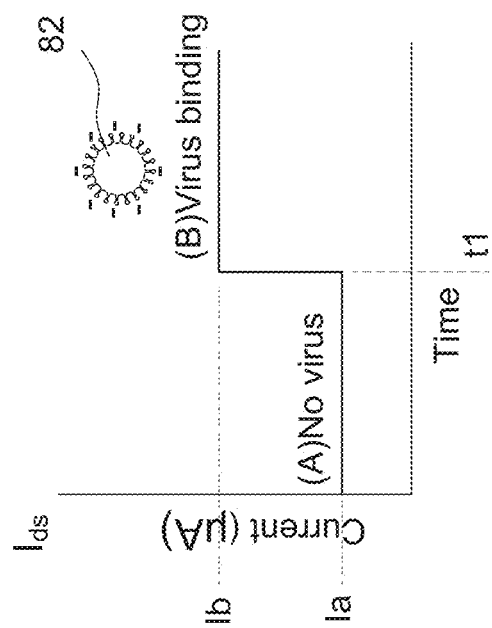

FIGS. 5A, 5B and 5C illustrate exemplary operations during biomolecule detection, in accordance with some embodiments of the present disclosure.

The devices 100, 120 and 140 shown in FIGS. 1A, 1B and 3A can be utilized in the detection of various types of target biomolecules. As shown in FIG. 5A, coating layers 501 and 502 can be disposed on the sensing film 48 before the detection commences. The coating layers 501 and 502 may provide receptor molecules 80 for binding the target biomolecules.

Depending on the types of target biomolecules, coating layers 501 and 502 can be disposed on the sensing film 48.

In some embodiments, the coating layer 501 may include one or more of Poly-1-lysine, 3-Aminopropyltriethoxysilane, or (3-Aminopropyl)trimethoxysilane.

In some embodiments, if the target biomolecules to be detected/sensed by the devices 100, 120 and 140 is RNA, the coating layer 502 can include microRNA. In some embodiments, if the target biomolecules to be detected/sensed by the devices 100, 120 and 140 is RNA, the coating layer 502 can include enzymes. In some embodiments, if the target biomolecules to be detected/sensed by the devices 100, 120 and 140 is DNA, the coating layer 502 can include DNA probes. In some embodiments, if the target biomolecules to be detected/sensed by the devices 100, 120 and 140 is DNA, the coating layer 502 can include aptamer probes. In some embodiments, if the target biomolecules to be detected/sensed by the devices 100, 120 and 140 are antigens, the coating layer 502 can include antibody probes. In some embodiments, if the target biomolecules to be detected/sensed by the devices 100, 120 and 140 are antibodies, the coating layer 502 can include antigen probes.

The coating layer 501 can be formed by first soaking the sensing film 48 with solutions including one or more of Poly-1-lysine, 3-Aminopropyltriethoxysilane, or (3-Aminopropyl)trimethoxysilane, and then washing the sensing film 48 with a buffer solution such as Phosphate-buffered saline (PBS). The coating layer 502 can be formed by first soaking the sensing film 48 with solutions including one or more of microRNA, enzymes, DNA probes, aptamer probes, antibody probes, or antigen probes, and then washing the sensing film 48 with a buffer solution such as PBS.

Referring to FIG. 5B, after analyte solution 54 that includes the target biomolecules 82 is filled within the tank formed by the separating structure 18, the target biomolecules 82 will gradually bind to the receptor molecules 80. FIG. 5C shows a change to the sensor current ($I_{ds}$) at the timing t1. Before the target biomolecules 82 bind to the receptor molecules 80 at the timing t1, the sensor current has an average value of Ia. After the target biomolecules 82 bind to the receptor molecules 80 at the timing t1, the sensor current has an average value of Ib. The difference between the average values Ia and Ib can be a basis for determining whether the target biomolecules 82 exist within the analyte solution 54.

In some embodiments, a threshold can be predetermined for biomolecule detection. For example, a threshold having a value between the values Ia and Ib can be set to determine whether the target biomolecule is detected. The threshold for biomolecule detection can be determined based on the values Ia and Ib. The value Ia can be referred to as a baseline value. The threshold for biomolecule detection can be associated with the value Ia. The threshold for biomolecule detection can be associated with the value Ib. The threshold for biomolecule detection can be associated with a difference between the values Ia and Ib.

It should be noticed that, the waveform of the current shown in FIG. 5C is for illustrative purposes; however, in some other embodiments, the average value Ia can be greater than the average value Ib. In some embodiments, the binding of the biomolecules 82 to the receptor molecules 80 may increase the magnitudes of the electrical signals outputted by the sensor. In some embodiments, the binding of the biomolecules 82 to the receptor molecules 80 may decrease the magnitudes of the electrical signals outputted by the sensor.

Referring back to FIG. 1A, the sensing regions 20a1, 20a2 and 20a3 can be used to detect different biomolecules. In the condition that the sensing regions 20a1, 20a2 and 20a3 are utilized to detect different target biomolecules, the type of coating layers disposed on the sensing regions 20a1, 20a2 and 20a3 can be different. For example, if the sensing region 20al is utilized to detect RNA, the coating layers disposed on the sensing region 20al may include microRNA and one of Poly-1-lysine, 3-Aminopropyltriethoxysilane, or (3-Aminopropyl)trimethoxysilane. Alternatively, if the sensing region 20a2 is utilized to detect antigens, the coating layers disposed on the sensing region 20a2 may include antibody probes and one of Poly-1-lysine, 3-Aminopropyltriethoxysilane, or (3-Aminopropyl)trimethoxysilane. In addition, if the sensing region 20a3 is utilized to detect another RNA, the coating layers disposed on the sensing region 20a3 may include enzyme and one of Poly-1-lysine, 3-Aminopropyltriethoxysilane, or (3-Aminopropyl) trimethoxysilane.

Referring back to FIG. 4, the channels 60a and 60b can be utilized to detect different target biomolecules. In the condition that the channels 60a and 60b are utilized to detect different target biomolecules, the type of coating layers disposed on the first portion 58a of the sensing film 58 can be different from the type of coating layers disposed on the second portion 58b of the sensing film 58. For example, if the channel 60a is utilized to detect RNA, the coating layers disposed on the first portion 58a of the sensing film 58 may include microRNA and one of Poly-1-lysine, 3-Aminopropyltriethoxysilane, or (3-Aminopropyl)trimethoxysilane. Alternatively, if the channel 60b is utilized to detect antigens, the coating layers disposed on the second portion 58b of the sensing film 58 may include antibody probes and one of Poly-1-lysine, 3-Aminopropyltriethoxysilane, or (3-Aminopropyl)trimethoxysilane.

The coating layers disposed on the sensing film 58 are associated with the type of target biomolecule. The coating layers disposed on the sensing film 58 depend on the type of target biomolecule.

Figure 6:
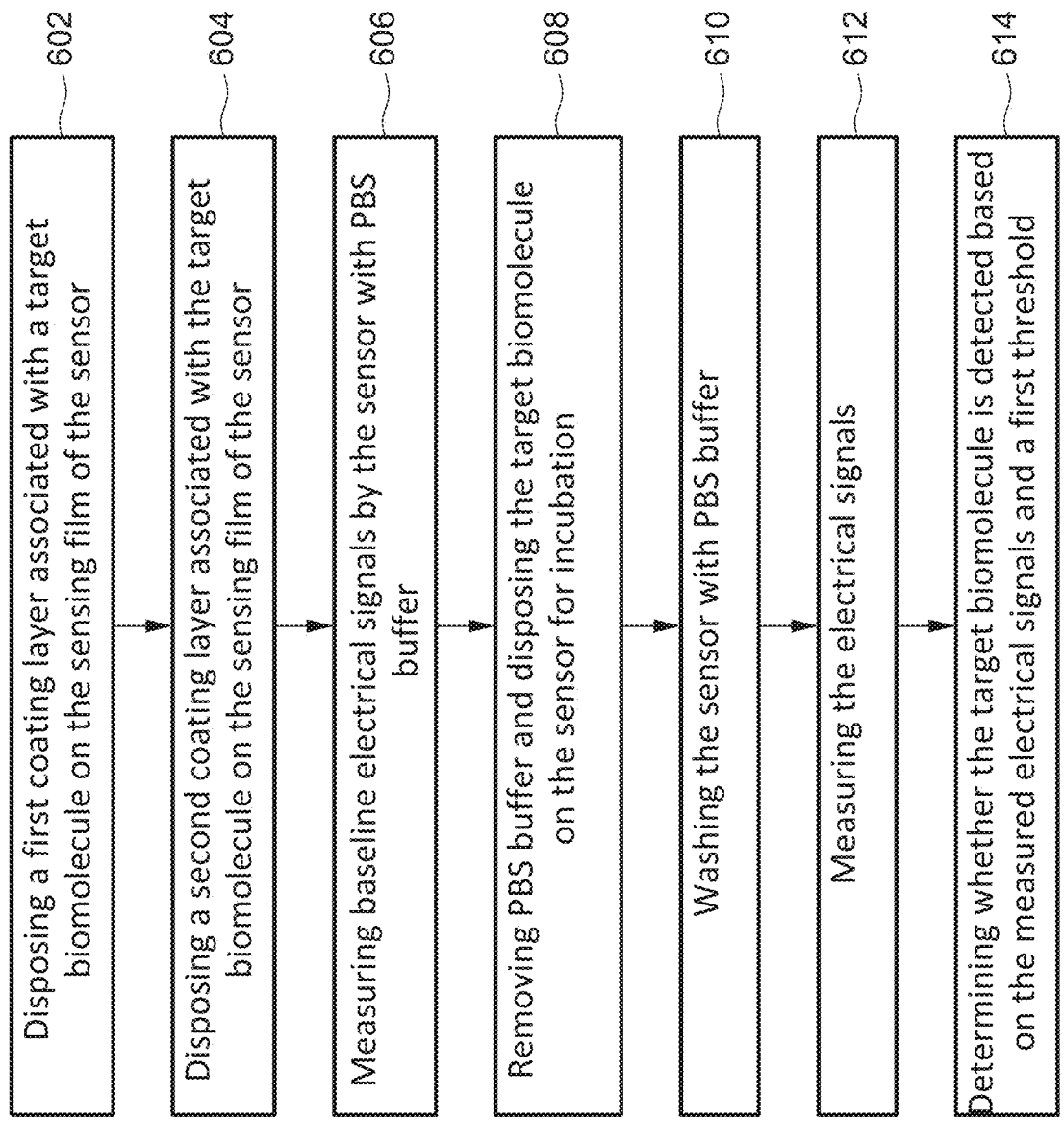
FIG. 6 illustrates a flow chart including operations for detecting target biomolecules on the basis of electronic detection principles, in accordance with some embodiments of the present disclosure.

FIG. 6 illustrates a flow chart including operations for detecting target biomolecules on the basis of electronic detection principles, in accordance with some embodiments of the present disclosure. FIG. 6 shows a flow chart 600. The flow chart 600 includes operations 602, 604, 606, 608, 610, 612 and 614.

In the operation 602, a first coating layer associated with target biomolecules is disposed on the sensing film of a sensor. For example, referring to FIG. 5A, the coating layer 501 can be disposed on the sensing film 48. The materials of the first coating layer may depend on the type of target biomolecules to be detected.

In the operation 604, a second coating layer associated with target biomolecules is disposed on the sensing film of a sensor. For example, referring to FIG. 5A, the coating layer 502 can be disposed on the sensing film 48. The materials of the second coating layer may depend on the type of target biomolecules to be detected. In some embodiments, if the target biomolecules to be detected/sensed is RNA, DNA, antigen, or antibody, the coating layer 502 can include one or more of microRNA, enzymes, DNA probes, aptamers probes, antibody probes, or antigen probes.

In the operation 606, baseline electrical signals are measured. The baseline electrical signals can include current signals or voltage signals. The baseline electrical signals can be measured when the sensor is soaked solely with buffer solution, such as PBS. Referring to FIG. 5C, for example, the baseline electrical signals can be measured before the timing t1. The baseline electrical signals can be measured before the analyte solution 54 including target biomolecules is filled within the tank formed by the separating structure 18.

The baseline electrical signals can be utilized as a reference for determining whether the target biomolecules have been detected. In some embodiments, the baseline electrical signals can be utilized as a reference for determining a threshold. The threshold determined in accordance with the baseline electrical signals can be utilized for determining whether the target biomolecules have been detected.

In the operation 608, buffer solution, such as PBS, is removed from the tank formed by the separating structure 18, and then the analyte solution 54 including target biomolecules is provided on the sensor for incubation. Referring to FIG. 5B, for example, the target biomolecules 82 can gradually bind to the receptor molecules 80.

In the operation 610, the sensor is washed with a buffer solution, such as PBS. The biomolecules within the analyte solution 54 that are not bound to the receptor molecules 80 will be removed.

In the operation 612, the electrical signals outputted by the sensor can be measured. The measured electrical signals can be displayed, for example, on the screen of a computer.

In the operation 614, whether the target biomolecules are detected can be determined based on the measured electrical signals and a first threshold. In some embodiments, the target biomolecules can be determined to be detected if the measured electrical signals are greater the first threshold. In some embodiments, the target biomolecules can be determined to be detected if the measured electrical signals are smaller than the first threshold.

The techniques described above in the present disclosure provide various advantages over existing techniques of biomolecule detection. The techniques described above in the present disclosure provide a rapid detection with high sensitivity. In general, the techniques described above in the present disclosure have a sensitivity over 93%. Furthermore, the minimum amount of the target biomolecules that can be detected is around 0.01 fg/mL. The techniques described above in the present disclosure can be widely applied in routine and urgent cases of laboratory or Point of Care diagnostics. In addition, the techniques described above in the present disclosure can be applied to various types of disease diagnostics, for example, tumors, COVID-19 and Parkinson's disease.

Figure 7:
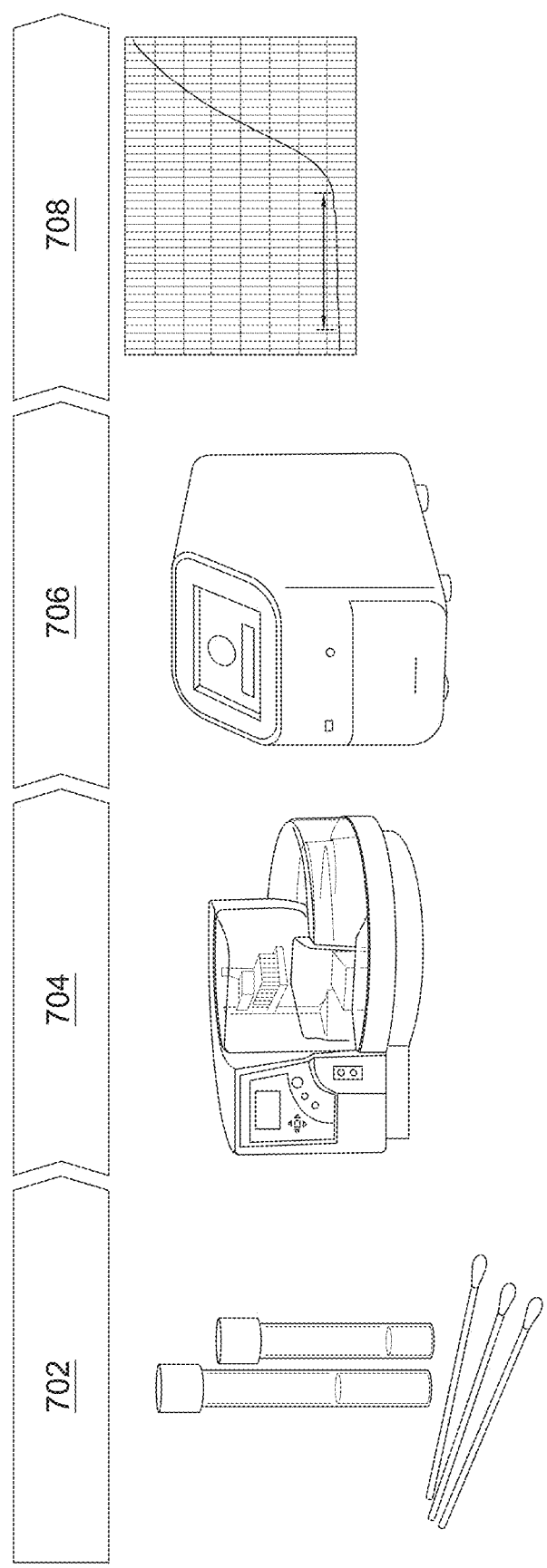
FIG. 7 illustrates operations for detecting target biomolecules on the basis of optical detection principles, in accordance with some comparative embodiments of the present disclosure.

FIG. 7 illustrates operations for detecting target biomolecule on the basis of optical detection principles, in accordance with some comparative embodiments of the present disclosure.

FIG. 7 includes operations 702, 704, 706 and 708 for detecting target biomolecule on the basis of optical detection principles.

In the operation 702, samples of target biomolecules are collected. The samples can be collected using, for example, swabs. In the operation 704, the samples collected can be prepared. In analytical chemistry, sample preparation refers to the ways in which a sample is treated prior to its analyses. Sample preparation may involve dissolution, extraction, reaction with some chemical species, pulverizing, treatment with a chelating agent (e.g., EDTA), masking, filtering, dilution, sub-sampling or many other techniques. Sample preparation could involve one or more of: crushing and dissolution, chemical digestion with acid or alkali, sample extraction, sample clean up and sample pre-concentration.

In the operation 706, a real-time polymerase chain reaction (real-time PCR) is performed. A real-time PCR, also known as quantitative Polymerase Chain Reaction (qPCR), is a laboratory technique of molecular biology based on the polymerase chain reaction (PCR). It monitors the amplification of a targeted DNA molecule during the PCR (i.e., in real time).

In the operation 708, data analysis is performed to determine whether the target biomolecules have been detected.

It should be noticed that the target biomolecules which can be detected by the operations shown in FIG. 7 merely include DNA or RNA. Although said operations have good detection sensitivity, they can be considerably time-consuming. Furthermore, the minimum amounts of the target biomolecules that can be detected cannot be less than 10 ng/mL.

Figure 8:
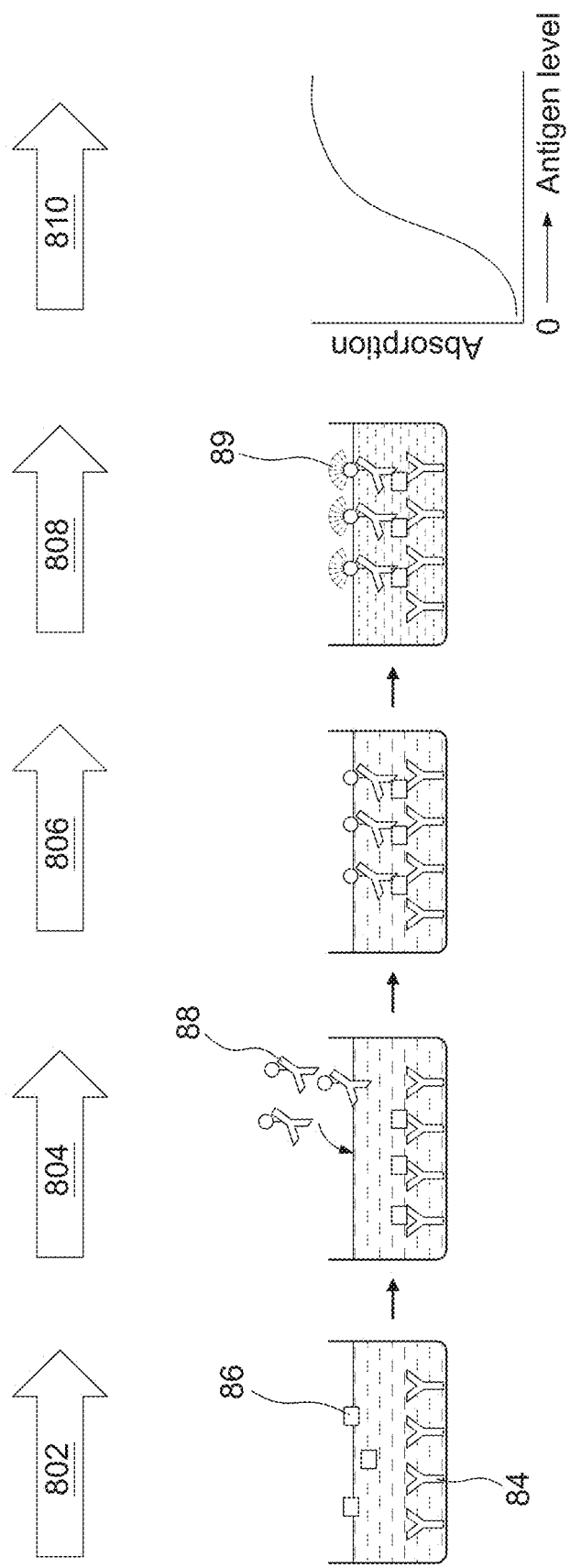
FIG. 8 illustrates operations for detecting target biomolecules on the basis of optical detection principles, in accordance with some comparative embodiments of the present disclosure.

FIG. 8 illustrates operations for detecting target biomolecule on the basis of optical detection principles, in accordance with some comparative embodiments of the present disclosure.

FIG. 8 includes operations 802, 804, 806, 808 and 810 for detecting target biomolecule on the basis of optical detection principles.

In the operation 802, antibody 84 for detecting the target protein 86 is immobilized on the surface of the microplate wells. In the operation 804, another antibody 88 specific to the target protein 86 is provided to the microplate wells. The antibody 88 is labeled with an enzyme. In the operation 806, the antibody 84, the target protein 86, and the antibody 88 labeled with an enzyme are incubated. In the operation 808, enzyme reaction 89 can be recognized on the antibody 88. In the operation 810, data analysis is performed to determine whether the target protein 86 has been detected.

It should be noticed that, the target biomolecules which can be detected by the operations shown in FIG. 8 merely include antibodies or antigens. Although said operations have good detection sensitivity, they can be considerably time-consuming. Furthermore, the minimum amounts of the target antibody that can be detected should be not less than 20 ng/mL, and the minimum amounts of the target antigen that can be detected cannot be less than 780 pg/mL.

Figure 9:
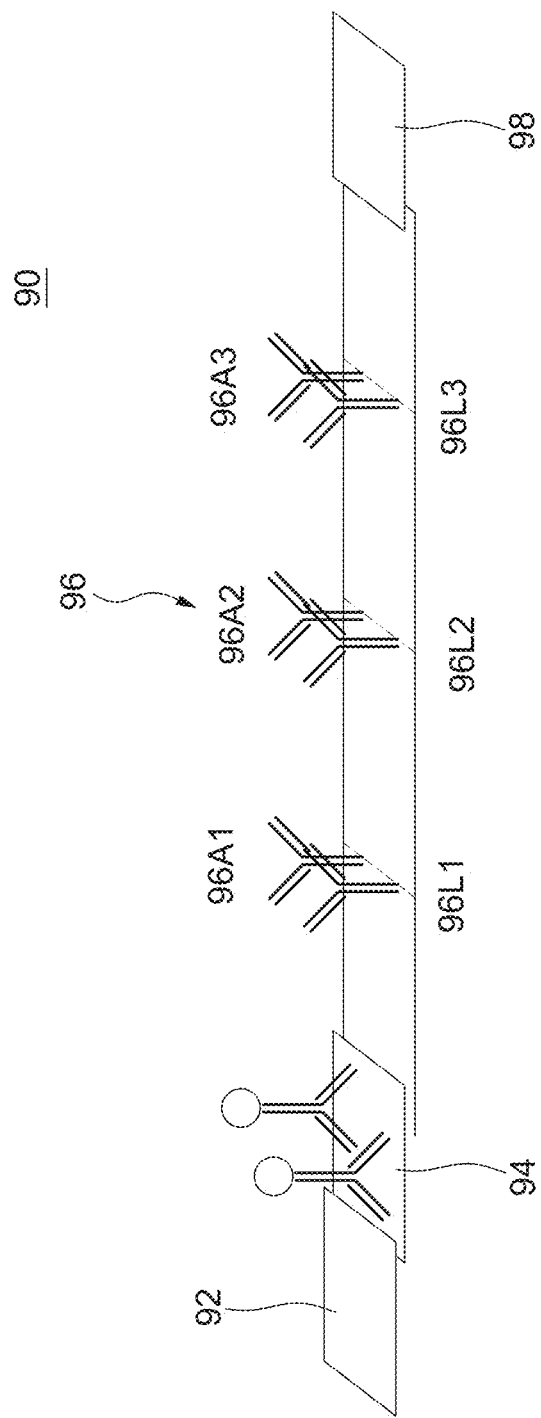
FIG. 9 illustrates a schematic diagram of a test strip for detecting target biomolecules, in accordance with some comparative embodiments of the present disclosure.

FIG. 9 illustrates a schematic diagram of a test strip for detecting target biomolecule, in accordance with some comparative embodiments of the present disclosure.

The test strip 90 includes a sample pad 92, a conjugate pad 94, a Nitrocellulose (NC) membrane 96, and an absorbent pad 98. The NC membrane 96 includes lines 96L1, 96L2 and 96L3. The line 96L1 can be immobilized with a first type of antibody 96A1. The line 96L2 can be immobilized with a second type of antibody 96A2. The line 96L3 can be immobilized with a third type of antibody 96A3. In some embodiments, the test strip 90 can be utilized for detecting snake venom proteins. In such embodiments, the antibody 96A1 can be associated with hemorrhagic venom, and the antibody 96A2 can be associated with neurotoxic venom. The line 96L3 can be a control line.

It should be noticed that the target biomolecules which can be detected by the test strip shown in FIG. 9 merely include antibodies or antigens. Although having the advantage of rapid detection, the test strip has a relatively low detection sensitivity. Furthermore, the minimum amounts of the target antibody that can be detected should not be less than 200 ng/mL, and the minimum amounts of the target antigen that can be detected cannot be less than 10 ng/mL.

Some embodiments of the present disclosure provide a method for detecting biomolecules. The method comprises disposing a first coating layer associated with a first target biomolecule on a first portion of a sensing film of a sensor and disposing a second coating layer associated with the first target biomolecule on the first portion of the sensing film. The method further comprising measuring a baseline electrical signal associated with a buffer solution by the sensor, disposing first analyte solution on the sensor, and measuring the first electrical signal associated with the first analyte solution. The method further comprises determining whether the first target biomolecule are detected in the first analyte solution based on a comparison between measured first electrical signal and a first threshold.

Some embodiments of the present disclosure provide a method for detecting biomolecules. The method comprises disposing a first coating layer associated with a first target biomolecule on a first region of a sensor, and disposing a second coating layer associated with the first target biomolecule on the first region of the sensor. The method further comprises disposing first analyte solution on first region of the sensor and measuring a first electrical signal associated with the first analyte solution. The method further comprises determining whether the first target biomolecule are detected in the first analyte solution based on measured first electrical signal.

Some embodiments of the present disclosure provide a system for detecting biomolecules. The system comprises a sensor and a separating structure surrounding a first region of the sensor. The sensor comprises: a substrate having a first side and a second side opposite to the first side; a first control gate disposed adjacent to the first side; and a second control gate disposed adjacent to the second side.

The foregoing outlines structures of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for detecting biomolecules, comprising:
    disposing a first coating layer associated with a first target biomolecule on a first portion of a sensing film of a sensor;
    disposing a second coating layer associated with the first target biomolecule on the first portion of the sensing film;
    measuring a baseline electrical signal associated with a buffer solution by the sensor;
    disposing a first analyte solution on the sensor and measuring the first electrical signal associated with the first analyte solution; and
    determining whether the first target biomolecule is detected in the first analyte solution based on a comparison between the measured first electrical signal and a first threshold,
    disposing a third coating layer associated with a second target biomolecule on a second portion of the sensing film of the sensor;
    disposing a fourth coating layer associated with the second target biomolecule on the second portion of the sensing film; and
    disposing a second analyte solution on the sensor and measuring a second electrical signal associated with the second analyte solution,
    wherein the second coating layer includes one or more of microRNA, enzyme, aptamer probes, antibody probes, or antigen probes.

2. The method of claim 1, further comprising washing the sensor with a buffer solution prior to measuring the first electrical signal associated with the first target biomolecule.

3. The method of claim 1, further comprising:
    determining whether the second target biomolecule is detected in the second analyte solution based on a comparison between the measured second electrical signal and a second threshold.

4. The method of claim 3, wherein the first electrical signal and the second electrical signal are measured by the sensor simultaneously.

5. The method of claim 3, wherein the first analyte solution is provided to the sensor through a first channel of a polydimethylsiloxane microfluidic system, and the second analyte solution is provided to the sensor through a second channel of the PDMS microfluidic system.

6. The method of claim 3, wherein the second coating layer and the fourth coating layer each includes one or more of microRNA, enzymes, DNA probes, aptamer probes, antibody probes, or antigen probes, and the second coating layer is different from the fourth coating layer.

7. The method of claim 1, wherein the sensor comprises:
a substrate having a first side and a second side opposite to the first side;
a first control gate disposed adjacent to the first side; and
a second control gate disposed adjacent to the second side.

8. The method of claim 7, wherein the sensor comprises an opening above the first control gate, and wherein a depth of the opening ranges from 0.5 microns to 3 microns.

9. The method of claim 1, wherein the first analyte solution is disposed within a tank surrounding the solution with a separating structure, and a depth of the separating structure ranges from 0.05 cm to 0.5 cm.

10. The method of claim 1, wherein the first coating layer includes one or more of Poly-1-lysine, 3-Aminopropyltriethoxysilane, or (3-Aminopropyl)trimethoxysilane.

11. The method of claim 1, wherein the second coating layer provides receptor molecules for binding the target biomolecules.

12. A method for detecting biomolecules, comprising:
disposing a first coating layer associated with a first target biomolecule on a first region of a sensor;
disposing a second coating layer associated with the first target biomolecule on the first region of the sensor;
disposing a first analyte solution on first region of the sensor and measuring a first electrical signal associated with the first analyte solution; and
determining whether the first target biomolecule is detected in the first analyte solution based on the measured first electrical signal,
disposing a third coating layer associated with a second target biomolecule on a second region of the sensor;
disposing a fourth coating layer associated with the second target biomolecule on the second region of the sensor; and
disposing a second analyte solution on the sensor and measuring a second electrical signal associated with the second analyte solution,
wherein the second coating layer includes one or more of microRNA, enzyme, aptamer probes, antibody probes, or antigen probes.

13. The method of claim 12, further comprising:
determining whether the second target biomolecule is detected in the second analyte solution based on the measured second electrical signal.

14. The method of claim 13, wherein the first region and the second region of the sensor are separated by a separating structure.

15. The method of claim 13, wherein the fourth coating layer includes one or more of microRNA, enzymes, DNA probes, aptamer probes, antibody probes, or antigen probes, and the second coating layer is different from the fourth coating layer.

16. The method of claim 13, wherein the first electrical signal and the second electrical signal are measured by the sensor simultaneously.

17. The method of claim 13, wherein the first region and the second region have different dimensions.

18. A system for detecting biomolecules, comprising:
a sensor which comprises:
a substrate having a first side and a second side opposite to the first side;
a first control gate disposed adjacent to the first side; and
a second control gate disposed adjacent to the second side;
a sensing film disposed on the sensor;
a first coating layer associated with a first target biomolecule on a first region of the sensing film of the sensor;
a second coating layer associated with the first target biomolecule on the first region of the sensing film;
a first analyte solution on the first portion of the sensor;
a third coating layer associated with a second target biomolecule on a second region of the sensor;
a fourth coating layer associated with the second target biomolecule on the second region of the sensor; and
a second analyte solution on the second region of the sensor; and
a separating structure surrounding a first region of the sensor.

19. The system of claim 18, further comprising:
a first electrode and a second electrode disposed in the substrate; and
a channel region between the first electrode and the second electrode;
wherein the first region is disposed above the channel region.

20. The system of claim 18, further comprising:
a first electrode and a second electrode disposed in the substrate;
a channel region between the first electrode and the second electrode; and
a polydimethylsiloxane microfluidic system attached to the sensor and including a first channel and a second channel isolated from the first channel;
wherein the first channel and the second channel are disposed above the channel region.

* * * * *